United States Patent [19]

Presant et al.

[11] Patent Number: 5,441,745
[45] Date of Patent: * Aug. 15, 1995

[54] METHOD OF DELIVERING MICELLULAR PARTICLES ENCAPSULATING CHEMOTHERAPEUTIC AGENTS TO TUMORS IN A BODY

[75] Inventors: Cary A. Presant, San Marino; Richard T. Proffitt, Arcadia; Raymond L. Teplitz, Pasadena; Lawrence E. Williams, San Dimas; George W. Tin, Arcadia, all of Calif.

[73] Assignee: Vestar, Inc., San Dimas, Calif.

[ * ] Notice: The portion of the term of this patent subsequent to May 28, 2008 has been disclaimed.

[21] Appl. No.: 663,550

[22] Filed: Oct. 22, 1984

Related U.S. Application Data

[63] Continuation-in-part of Ser. No. 363,593, Mar. 30, 1982, abandoned.

[51] Int. Cl.$^6$ ............................................. A61K 9/133
[52] U.S. Cl. ..................................... 424/450; 436/829
[58] Field of Search ........................... 424/1.1, 9, 450; 436/829

[56] References Cited

U.S. PATENT DOCUMENTS

| | | | |
|---|---|---|---|
| 3,932,657 | 1/1976 | Rahman | 514/1 |
| 3,957,971 | 5/1976 | Oleniacz | 424/70 |
| 3,992,513 | 11/1976 | Petkau et al. | 424/1.1 |
| 3,993,754 | 11/1976 | Rahman | 424/450 X |
| 4,016,290 | 4/1977 | Rahman | 514/1 |
| 4,186,183 | 1/1980 | Steck et al. | 424/38 |
| 4,193,983 | 3/1980 | Ullman et al. | 424/1.1 |
| 4,224,179 | 9/1980 | Schneider | 424/36 |
| 4,235,871 | 11/1980 | Papahadjopoulos et al. | 424/19 |
| 4,241,046 | 12/1980 | Papahadjopoulos et al. | 424/19 |
| 4,310,505 | 1/1982 | Baldeschwieler et al. | 424/1.1 |
| 4,310,506 | 1/1982 | Baldeschwieler et al. | 424/1.1 |
| 4,377,567 | 3/1983 | Geho | 424/1.1 |
| 4,497,791 | 2/1985 | Gamble et al. | 424/1.1 |
| 4,544,545 | 10/1985 | Ryan et al. | 424/1.1 |
| 5,019,369 | 5/1991 | Presant et al. | 424/1.1 |

FOREIGN PATENT DOCUMENTS 2249552 10/1972 Germany ........................... 424/450

OTHER PUBLICATIONS

Proffitt et al, J. Nuclear Medicine, 24(1), pp. 45–51 (1983).
Mauk et al, Proc. National Academy Sci. USA, 76(2), pp. 765–769 (1979).
Wu et al, Proc. National Academy Sci. USA 78(4), pp. 2033–2037 (1981).
Richardson et al, J. Nuclear Medicine, 19(9), pp. 1049–1054 (1978).
Barsy et al., *Laboratory Investigation*, vol. 34(3), 273–82.
Espinola, L. G., *J. Nuclear Medicine*, vol. 20(5), 434–40 (1979).
Hwang et al., *Proc. Nat. Academy of Sciences*, vol. 11, 4991–95 (1977).
Proffitt, R. T. et al., *Proc. American Association Cancer Research*, vol. 2, 41 (1981).

(List continued on next page.)

*Primary Examiner*—Gary Geist
*Assistant Examiner*—Lara E. Chapman

[57] ABSTRACT

A method is provided for delivering micellular particles containing chemotherapeutic agents and a marker to tumors within a body for the diagnosis and treatment of such tumors. The micellular particles are small, less than 2000 Å and incorporate pure, neutral phospholipid molecules in their external surface. Enhanced delivery of the micellular particles containing marker and chemotherapeutic agents may be achieved by introducing an initial group of positively charged micellular particles to block the reticuloendothelial cells present in the body.

17 Claims, 7 Drawing Sheets

OTHER PUBLICATIONS

Proffitt, R. T. et al., *Science*, vol. 220(2), 502–04 (1983).
Anighileri et al., *J. Nucl. Biol. Med.*, 20, 165–67 (1976).
Richardson et al., *Brit. J. Cancer*, 40, 35–43 (1979).
M. R. Mauk et al., *Science*, 207, 309–11 (1980).
Chemical Abstracts, vol. 92, 1980, p. 339, Abstract No. 169129; R. S. Chawla, "The Effect of Liposomal Charge on Drug Toxicity and Efflux", *J. Pharm. Pharmacol*, 1979 31 Supp. (Br. Pharm. Conf. 1979).
Chemical Abstracts, vol. 99, No. 6, (1983), 306–07, Abstract No. 433935, P. Machy et al. "Small Liposomes are Better than Large Liposomes for Specific Drug Delivery in Vitro" Biochmim. Biophys. Acta. 1983 730(2), 313–20.
Chemical Abstracts, vol. 93, No. 26, (1980), p. 382, Abstract No. 245393d, Gregoriadis et al., "The Phospholipid Component of Small Unilamellar Liposomes Controls the Rate of Clearance of Entrapped Solutes from the Circulation", Febs. Lett. 1980, 119(1), 43–6.
Chemical Abstracts, vol. 99, 1983, p. 314, Abstract No. 43459t, White et al., "The Influence of Cholesterol on the Stability of Liposomes Containing Methotrexate", *Biochem. Soc. Trans.*, 1983, 11(3), 305–06.

| ORGAN | % INJECTED DOSE PER GRAM OF TISSUE (± S.D) | | | |
|---|---|---|---|---|
| | FREE ¹¹¹In-NTA (n=2) | ¹¹¹In-NTA DS PC:Ch (n=4) | ¹¹¹In-NTA DS PC:Ch:SA (n=4) | ¹¹¹In-NTA DS PC:Ch:DP (n=4) |
| TUMOR | 2.4 | 18.5 ± 4.7 | 6.2 ± 2.1 | 11.9 ± 2.0 |
| BLOOD | 0.30 | 6.6 ± 1.6 | 0.95 ± 0.34 | 13 ± 0.4 |
| LIVER | 3.1 | 14.6 ± 1.7 | 28.5 ± 2.2 | 16.6 ± 1.6 |
| SPLEEN | 2.5 | 18.8 ± 3.3 | 43.8 ± 5.2 | 39.3 ± 3.4 |
| KIDNEY | 10.8 | 6.8 ± 0.6 | 6.8 ± 0.6 | 12.7 ± 3.5 |
| LUNG | 1.8 | 6.0 ± 1.5 | 1.8 ± 0.1 | 3.0 ± 0.5 |
| BONE | 2.4 | 3.9 ± 1.5 | 2.6 ± 0.6 | 4.8 ± 0.5 |

FIG. 1

| ORGAN | % INJECTED DOSE PER GRAM OF TISSUE (± S.D) | | |
|---|---|---|---|
| | DS PC:Ch:AM (4:1:1) AM (n=2) | DS PC:Ch:AM (8:3:1) AM/2 (n=3) | DS PC:Ch:AML (4:1:1) AML (n=3) |
| TUMOR | 0.91 | 1.0 ± 0.5 | 1.7 ± 0.2 |
| BLOOD | 0.23 | 0.24 ± 0.07 | 0.30 ± 0.02 |
| LIVER | 29.6 | 40.5 ± 6.9 | 17.4 ± 1.4 |
| SPLEEN | 49.0 | 74.4 ± 28.6 | 56.0 ± 10.9 |
| KIDNEY | 4.62 | 2.5 ± 0.5 | 6.5 ± 1.0 |
| LUNG | 3.2 | 1.5 ± 0.9 | 4.7 ± 2.0 |
| BONE | 1.7 | 1.2 ± 0.6 | 3.0 ± 0.5 |

FIG. 2

| TISSUE | DS PC:Ch:AM (8:3:1) (AM/2) BLOCKADE | In ¹¹¹In-NTA DS PC:Ch (2:1) | In ¹¹¹In-NTA DS PC:Ch:SA (4:1:1) | In ¹¹¹In-NTA DS PC:Ch:DP (4:1:1) |
|---|---|---|---|---|
| TUMOR | + | 26.4 | 11.8 | 11.7 |
|  | − | 18.5 | 6.1 | 11.9 |
| LIVER | + | 10.2 | 17.6 | 17.3 |
|  | − | 14.6 | 28.5 | 16.6 |
| SPLEEN | + | 10.5 | 32.4 | 32.7 |
|  | − | 18.8 | 43.8 | 39.3 |
| LUNG | + | 8.0 | 2.8 | 3.8 |
|  | − | 6.0 | 1.8 | 3.0 |
| KIDNEY | + | 6.6 | 7.8 | 17.8 |
|  | − | 6.8 | 6.8 | 17.1 |
| BLOOD | + | 7.9 | 2.4 | 1.7 |
|  | − | 6.6 | 1.0 | 1.3 |

FIG.3

| TREATMENT | [³H] MTX IN TUMOR (dpm/gm) | TREATMENT CONTROL | [14C] LIPID IN TUMOR (dpm/gm) |
|---|---|---|---|
| FREE [³H] MTX | 6,700 | 1.0 | — |
| LIPOSOME ENTRAPPED [³H] MTX | 20,150 | 3.0 | 12,570 |
| LIPOSOME ENTRAPPED [³H] MTX; AFTER AM/2 BLOCKADE | 19,000 | 2.8 | 12,670 |

FIG.4

| TISSUE | % INJECTED DOSE / GRAM TISSUE | | |
|---|---|---|---|
| | FREE $^{111}$In-EDTA | $^{111}$In-EDTA IN VESICLES | [14C] - DPPC IN VESICLES |
| TUMOR | 0.050 | 7.94 | 9.16 |
| BLOOD | 0.006 | 5.53 | 4.28 |
| HEART | 0.006 | 1.02 | 1.75 |
| LUNG | 0.024 | 2.40 | 3.12 |
| LIVER | 0.025 | 11.29 | 12.70 |
| SPLEEN | 0.033 | 9.71 | 7.57 |
| KIDNEY | 0.098 | 3.41 | 4.02 |

FIG.7

| TISSUE | EMT6 TUMOR IN BALB/c | COLON 51 CARCINOMA IN BALB/C | B16 MELANOMA IN C57/B16 | MAMMARY CARCINOMA 16/c IN C34 | % INJECTED DOSE/GRAM TISSUE SARCOMA 180 IN SWISS-WEBSTER | COLON 38 ADENO CARCINOMA IN C57/B16 | PANCREATIC DUCT 02 CARCINOMA IN C57/B16 | LEWIS LUNG CARCINOMA IN C57/B16 | OVARIAN CARCINOMA M5 IN C57/B16 | OSTEOGENIC SARCOMA |
|---|---|---|---|---|---|---|---|---|---|---|
| BLOOD | 2.9 | 8.1 | 6.9 | 1.1 | 5.6 | 0.9 | 1.4 | 4.0 | 4.1 | 4.0 |
| TUMOR | 22.0 | 17.8 | 10.4 | 17.3 | 11.2 | 4.3 | 23.4 | 17.2 | 12.8 | 8.6 |
| LIVER | 23.1 | 20.0 | 26.8 | 19.4 | 10.5 | 35.3 | 32.6 | 29.5 | 25.9 | 22.6 |
| SPLEEN | 20.9 | 30.5 | 34.5 | 36.1 | 14.1 | 23.2 | 29.1 | 27.7 | 29.3 | 22.3 |
| KIDNEY | 6.9 | 9.5 | 8.6 | 5.5 | 6.8 | 7.8 | 11.7 | 7.7 | 8.3 | 8.4 |
| LUNG | 2.3 | 3.9 | 6.0 | 3.4 | 2.7 | 2.0 | 3.5 | 11.6 | 2.7 | 3.2 |
| BONE | 3.3 | 2.6 | 4.6 | 1.9 | 2.5 | 4.0 | 5.0 | 3.9 | 3.6 | 4.0 |
| MUSCLE | 2.2 | 0.9 | 0.9 | 0.4 | 1.0 | 0.7 | 0.9 | 0.8 | 0.9 | 0.7 |
| SKIN | 5.5 | ND | ND | ND | ND | ND | 3.8 | 4.5 | ND | ND |
| INTESTINE | 3.4 | 2.7 | 3.6 | 1.9 | 2.2 | 2.3 | 3.6 | 2.5 | 2.3 | 3.2 |

FIG.8

METHOD OF DELIVERING MICELLULAR PARTICLES ENCAPSULATING CHEMOTHERAPEUTIC AGENTS TO TUMORS IN A BODY

This application is a continuation-in-part of application Ser. No. 363,593 filed Mar. 30, 1982, now abandoned.

BACKGROUND

1. Field of the Invention

This invention relates to methods for delivering micellular particles to tumor cells in a body. More particularly, the invention relates to methods of introducing neutral or charged phospholipid micellular particles containing chemotherapeutic agents and a marker into a patient's body to diagnose and treat such tumors.

2. Description of Prior Art

Before various abnormalities such as tumors in a patient's body can be diagnosed and treated, it is often necessary to locate the abnormalities. This is particularly true of such abnormalities as malignant tumors Since-the treatment of such tumors is often on a localized basis. For example, the location of malignant tumor cells has to be identified so that a chemotherapeutic agent can be directed to such cells to eliminate the tumor.

Various attempts have been made over an extended number of years to identify specific locations, such as tumor locations, in a patient's body by simple techniques. For example, it would be desirable for diagnostic purposes to identify the location of cancer cells in a patient's body by a simple method involving the introduction of particular mobile particles to the patient's body and the movement of such particles to the cancer cells. It would also be desirable to treat such cancer cells by introducing chemotherapeutic agents into the patient's body and having such agents move to such specific locations to combat the cancer cells at such locations. In spite of such attempts over extended periods of time, simple methods of targeting specific locations, such as tumors for diagnosis, and methods for delivering chemotherapeutic agents to the tumors in a patient's body for treatment do not exist as yet.

Placing a chemotherapeutic drug in the body orally, subcutaneously or intravenously can result in harm to the normal cells in the body which take up the drug and a worsening in the patient's condition, without achieving the desired reduction in tumor cell activity. In the past, this toxicity to normal cells in the patient's body has been a major disadvantage in the treatment of tumors with chemotherapeutic agents. The lack of efficacy of such chemotherapy is also attributable to the failure of the freely circulating drug to localize within tumor cells before it is excreted or taken up by other cells in the body.

Prior attempts to improve treatment of tumors by chemotherapeutic agents have included encapsulation of such agents within biodegradable phospholipid micellular particles in the form of vesicles or liposomes. Encapsulation is thought to reduce the potential toxicity from the circulating drugs. Researchers have also sought to utilize such encapsulation to selectively target tumors within a body for delivery of chemotherapeutics. However, until the invention disclosed in the present application and the related application Ser. No. 363,593, abandoned, such efforts to reliably place drug-encapsulating particles within tumor cells has not been demonstrated.

Because solid tumors and their metastases are located in extravascular tissues, to accomplish targeting of intravenously injected chemotherapeutic agents to the tumor cells, the agents must leave the normal circulation by crossing blood vessel membranes to enter the extra-vascular tissues. This movement is known as "extravasation". In addition the encapsulated agent must cross the tumor cell membrane. Normally, small substances such as small molecular weight proteins and membrane-soluble molecules can cross cell membranes by a process known as passive diffusion. However, passive diffusion will not allow sufficient accumulation of larger particles carrying drugs within cells to reach therapeutic levels. Additionally, cells can actively transport materials across the membrane by a process such as pinocytosis wherein extracellular particles are engulfed by the membrane and released inside the cell. Entry of encapsulating particles into individual cells may occur by pinocytosis.

Progress in targeting specific locations, such as tumor locations, with chemotherapeutic drugs encapsulated in particles such as vesicles has been hampered by the inability to achieve movement of encapsulated drug across blood vessel membranes and to detect such movement. In the usual case, large structures such as drug encapsulating vesicles cannot escape from blood vessels such as capillaries, and thus remain in the circulation. However, an examination of the structure of the vascular morphology of a tumor reveals that the various blood vessels associated with tumors, in particular capillaries, exhibit alterations in their structure as a result of tumor cell growth patterns. Studies of tumor capillary permeability suggest that these morphologic variations in the capillaries allow some substances to cross the capillary membrane. Such variations include defects in the vascular endothelium from poor cell differentiation, and breaks in vascular walls as a result of invading tumor cells. Examples of tumor-modified capillaries include vessels with interrupted endothelial lining and vessels with fenestrated endothelium. H. I. Peterson, *Vascular and Extravascular Spaces in Tumors: Tumor Vascular Permeability*, Chapter III, Tumor Blood Circulation, H. I. Peterson, Ed. (1979).

Notwithstanding such knowledge of tumor vascular morphology, researchers such as Peterson have concluded that transport of large molecules or materials across the tumor capillary wall occurs as a result of passive diffusion only and that "concentrations of active drugs sufficient for therapeutic effect are difficult to reach." Id. at 83.

Prior to such morphologic studies, early research on the problem of extravasation suggested that vesicles might undergo "transcapillary passage" across the capillary membranes and on into tumor cells. G. Gregoriadis, *Liposomes in Biological Systems*, Gregoriadis, Ed., Ch 2, (1980). However, available data indicated that the vesicles were unstable in vivo and that the radiolalel may have leaked, thus apparently prompting alternative theories such as prolonged circulation of vesicles and the release of drugs from such vesicles at a slower rate, and interaction of the liposomes with the capillary walls without actually crossing the wall surface, which presumably resulted in the drugs being detected within tumors. Id. Other researchers simply have concluded that the vesicles do not penetrate vascular walls after intravenous administration. B. Ryman et al., *Biol. Cell,*

Vol. 47, pp. 71–80 (.983); G. Poste, Biol. Cell, Vol. 47, pp. 19–38 (1983).

Thus, although the prior art has recognized the necessity that vesicles carrying therapeutic drugs must cross vascular barriers to reach tumor cells, the experience of the art has taught that intravenous administration of micellular particles such as phospholipid vesicles is not effective to deliver encapsulated drugs to extravascular tumor cells.

This invention provides simple methods of enhancing extravasation of encapsulated chemotherapeutic agents to tumor cells within a body. The method of this invention further provides for the identification of such tumor sites in the body. This invention also provides for the delivery of chemotherapeutic agents to the cells of such tumors to combat such tumors.

SUMMARY OF THE INVENTION

The methods of this invention include the provision of biodegradable micellular particles. Micelles are water-soluble aggregates of molecules with hydrophobic and hydrophilic portions (so-called amphiphilic molecules) which associate spontaneously. Such micelles can be in the form of small spheres, ellipsoids or long cylinders, and can also consist of bilayers with two parallel layers of amphiphilic molecules. Such bilayered micelles usually take the shape of spherical vesicles with an internal aqueous compartment. Useful compositions of these micelles include phospholipid molecules in the structure. Small, single-layered vesicles generated by sonication of bimolecular layers of lipid molecules are known as liposomes.

The present invention contemplates use of small (less than 2000 Å), micellular particles in the form of phospholipid vesicles. Pure (more than approximately 98% pure) neutral phospholipid molecules are incorporated into the vesicles. However, micellular particles in other than spherical form and/or incorporating a phospholipid substitute may also be used. The phospholipid molecules or internal contents of the particles may be labeled as by radioactivity to detect the location of the particles within the body. Additionally, chemotherapeutic agents may be associated with the phospholipid molecules or internal contents of the particles to treat the tumors.

The phospholipid molecules may constitute distearoyl phosphatidylcholine (DSPC). The stability of the distearoyl phosphatidylcholine particles may be enhanced by the incorporation of cholesterol into the particles. Positively charged molecules such as stearylamine or aminomannose or aminomannitol derivatives of cholesterol or negatively charged molecules such as dicetyl phosphate may also be incorporated into the micellular particles.

When the phospholipid vesicles are introduced into the blood stream of a patient, they move to specific locations in the patient's body. The specific locations may be those where cancerous growths such as tumors are located. The cancerous growths at the specific locations may then be identified and treated. For example, chemotherapeutic drugs may be included in the phospholipid vesicles and such drug-bearing vesicles may then be introduced into the patient's body for targeting to the tumor locations in the body.

To enhance the movement of the phospholipid vesicles to the tumors in the patient's body, first positively charged phospholipid vesicles may be introduced into the patient's blood stream to block uptake by the reticuloendothelial cells of the liver, spleen and other tissues in the patient's body. The positively charged molecules bound to such phospholipid vesicles may be aminomannose or aminomannitol derivatives of cholesterol. Concurrently, or after a suitable period of time such as approximately one (1) hour, other phospholipid vesicles may be introduced into the patient's blood stream to move to the specific locations such as tumors in the patient's body. Such phospholipid vesicles preferably are neutral, may include cholesterol and may be positively charged as by the inclusion of a stearylamine or aminomannose or aminomannitol derivatives of cholesterol, or may be negatively charged as by the inclusion of dicetyl phosphate.

When the phospholipid vesicles are introduced into the body to target tumors, Indium-111 may be used as the labelling agent. The Indium-111 may be chelated to a suitable material such as nitrilotriacetic acid (NTA). NTA is advantageous because it forms a weak bond with the Indium-111. As a result, when the phospholipid vesicles reach the tumor, the nitrilotriacetic acid is displaced by proteins at the tumor. Since the proteins form a strong bond with the Indium-111, the Indium-111 remains at the tumor for a long period of time in excess of 24 hours. This provides for an easy identification of the tumor over an extended period of time.

IN THE DRAWINGS:

FIG. 1 is a table illustrating the targeting of phospholipid vesicles to tumors in a body;

FIG. 2 is a table illustrating the targeting and blocking of reticuloendothelial cells in the liver and spleen by phospholipid vesicles;

FIG. 3 is a table illustrating the targeting of phospholipid vesicles to tumors in the body after the blocking of the reticuloendothelial cells in the liver and spleen; and FIG. 4 is a table illustrating the enhanced delivery of drugs to a tumor in a body by the use of phospholipid vesicles.

FIG. 7 is a table illustrating the blood distribution of neutral labelled vesicles incorporating $^{111}$In- EDTA or 14C-Dipalmitoyl phosphatidylcholine as compared to the $^{111}$In-EDTA in various tissues.

FIG. 8 is a table illustrating the blood distribution of labelled phospholipid vesicles in tissues of mice bearing 10 different tumors.

MATERIALS AND METHODS

Liposome Preparation

Figure 5:
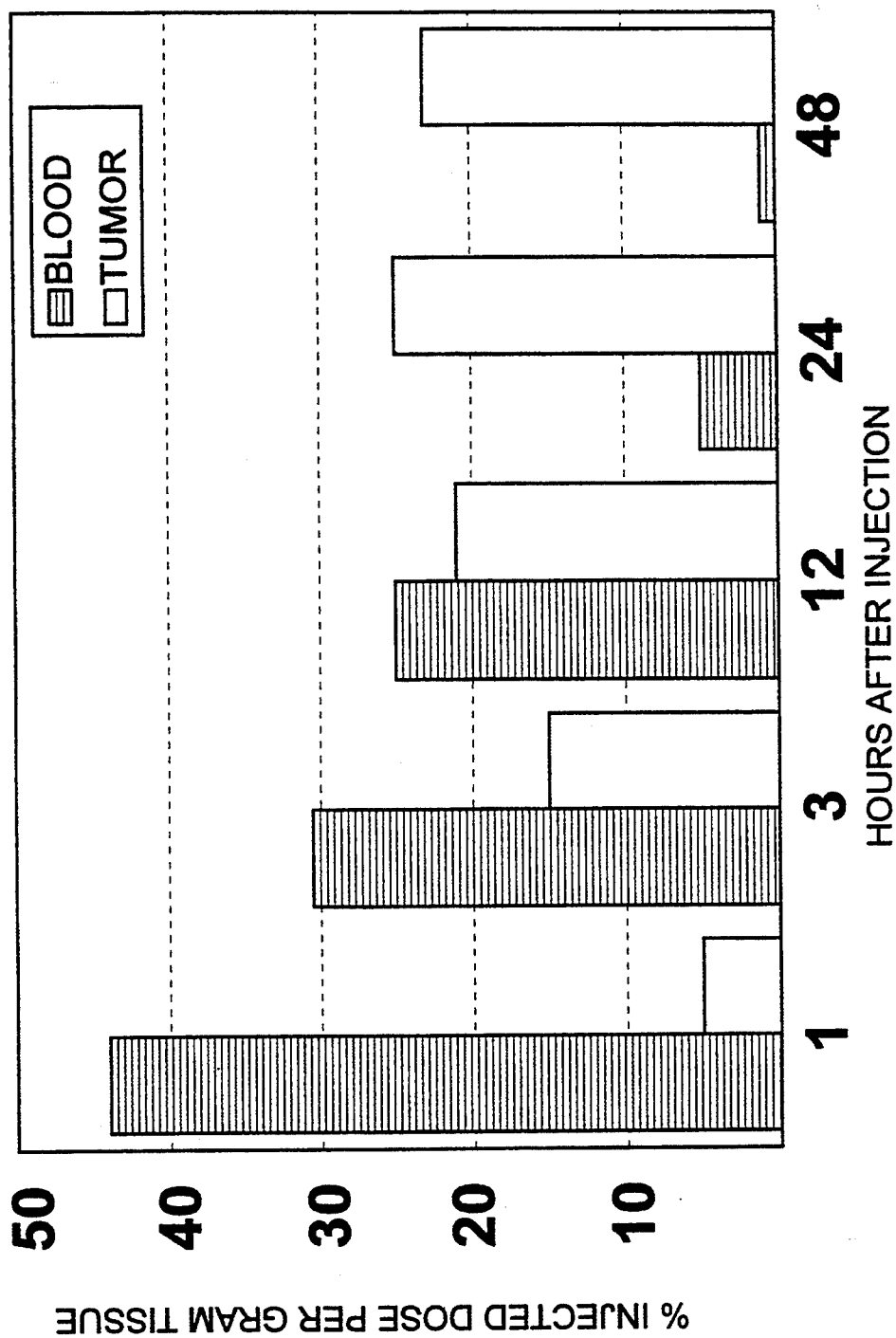
FIG. 5 is a chart illustrating the time course of clearance of radiolabelled phospholipid vesicles in blood and tumor.

Small unilamellar vesicles (SUV) with the ionophore A23187 were prepared from distearoyl phosphatidylcholine (DSPC), cholesterol (Ch), dicetyl phosphate (DP), stearylamine (SA) and the 6-aminomannose (AM), and 6-aminomannitol (AML) derivatives of cholesterol, according to previous methods. Briefly, chloroform solutions of 10 mg lipid with the following molar ratios: DSPC:Ch, 2:1; DSPC:Ch:X, 4:1:1 where X=SA, DP or AML; and DSPC:Ch:AM, 8:3:1, were evaporated to dryness under nitrogen ($N_2$) and further dried under vacuum overnight. Each tube was filled with 0.6 ml phosphate 10 mM phosphate buffered 0.9 saline, pH 7.4 (PBS), containing 1 mM nitrilotriacetic acid (NTA) and sonicated under $N_2$ for 5 to 15 minutes with a MSE sonicator equipped with a titanium microtip. Sonication yielded the small, unilamellar vesicles or liposomes used throughout these experiments.

Liposomes were annealed at 60° C. for 10 minutes and centrifuged at 300×g. Liposomes were separated from unencapsulated NTA with a 30×1.5 cm Sephadex G-50 column. Liposome size was determined by electron microscopy of preparations negatively stained with uranyl acetate. All vesicle types were shown by electron microscopy to have a mean diameter less than 0.1 microns (1000 Å). For example, DSPC:Ch vesicles had a mean diameter of approximately 528 Å. However, vesicles as large as approximately 2000 Å are believed to be satisfactory in obtaining the desired results of this invention.

The vesicles obtained as described above are chemically pure. By "chemically pure" is meant that the materials which constitute phospholipid vesicles are more than 98% pure. For example, when the phospholipid chemical added is distearoyl phosphatidylcholine, this material is used at more than 98% purity. The same constraint holds for other components, such as cholesterol, which compose the vesicle. The phospholipid vesicles obtained as described above are stable when injected into experimental animals.

The aminomannose and aminomannitol derivatives of cholesterol extend externally from the phospholipid vesicles. These materials and cholesterol tend to impart stability to the phospholipid vesicles. Cholesterol may be included in the range of approximately 0% to 50% of cholesterol by weight the remainder constituting the phospholipids. The charged molecules such as the stearylamine, the dicetyl phosphate and the aminomannose and aminomannitol derivatives of cholesterol may be included in the range of 0% to 20% by weight of the charged molecules the remainder constituting the phospholipids. The aminomannose derivative of cholesterol may constitute 6-(5-cholesten-3B-yloxy) hexyl-6-amino-6-deoxy-1-thio-&-D-mannopyranoside.

The chemically pure liposome compositions discussed above are quite stable to leakage in vitro and in vivo. However, phospholipid mixtures such as egg lecithin form more fluid membranes than pure phospholipids. As a result, liposomes from natural lecithin mixtures are less stable to leakage of their contents than pure phospholipids. However, liposomes from natural lecithin mixtures may also be used in the methods of this invention, particularly when results not as clear-cut as the results obtained from pure phospholipids may be considered to be adequate.

In-111 Loading Procedure

Loading of In-111 into preformed liposomes was facilitated by the presence of the ionophore A23187 in the lipid bilayer. In-111 was loaded into liposomes at 60°–80° C. as described. Incubations were terminated by the addition of 10 mM ethylenediaminetetraacetic acid (EDTA) in 10 mM phosphate buffered 0.9% sodium chloride, pH 7.4 (PBS), and free In-111 was separated from the loaded liposomes by chromatography on Sephadex G-50. Up to 90% of the added In-111 could be incorporated into preformed liposomes by this technique, and specific activities of up to 300 μCi/mg lipid have been obtained.

EMT6 Tumor Growth

Male BALB/c mice weighing 20–25 g were injected subcutaneously on the right hind leg with 5×10⁵ EMT6 cells in 0.1 ml sterile phosphate buffered saline. Tumors were allowed to grow for 10–20 days prior to using these animals for imaging studies. At this stage, tumors weighed between 0.2 and 0.4 gm. Up to 0.5 ml PBS containing 1 to 2 mg liposomes loaded with up to 30 μCi In-111 were injected into the tail vein of each animal. Control animals were injected with In-111-NTA which had not been encapsulated in liposomes.

Gamma Camera Imaging

At one (1) hour and at twenty-four (24) hours after injecting In-111 loaded liposomes, each animal was anesthetized with 40 mg/kg sodium pentobarbital and positioned on a platform 12 cm from the gamma scintillation camera equipped with a 6 mm pinhole. Whole-body dorsal images were acquired on x-ray film and corresponding digitized data were stored on magnetic discs for computer analysis.

Biodistribution of Radioactivity

Immediately after the twenty-four (24) hour images were acquired, animals were sacrificed and dissected to determine the organ distribution of radioactivity. Organs or tissues were excised, washed in PBS, blotted dry, and weighed. Radioactivity was measured in a well-type gamma-ray spectrometer and quantitated based on activity present in liposomes before injection. In some experiments, the gamma-ray perturbed angular correlation technique was used to measure the rotational correlation time of the In-111 in individual tissues and thereby assess the proportion of isotope remaining in intact liposomes.

Autoradiography

For autoradiography small, neutral, unilamellar vesicles were prepared with a composition similar to that described above for the In-111 labelling, except that 30 microcuries of [³H]-dipalmitoyl phosphatidylcholine ([³H]-DPPC) was added per mg total lipid as a marker and to produce autoradiographic exposure.

For autoradiographic studies, EMT6 tumor fragments (25–50 mg) were implanted subcutaneously in female BALB/C mice 5 to 12 days prior to the experiment. EMT6 tumor bearing mice were then given intravenous injections of 225–350 microcuries of [³H]-labelled vesicles, or normal saline as a background control. Fifteen hours later, when tumor uptake of isotope was maximal, the animals were sacrificed. Tumor, heart, skeletal muscle, liver, spleen and skin samples were removed, immediately immersed in the solution of 2% glutaraldehyde-2% paraformaldehyde, and sectioned into 1-2 mm pieces. The samples were further fixed in 1% osmium tetroxide, and then dehydrated and embedded in EPON for thin sectioning.

Thin (1.5 micron) tissue sections were placed on microscope slides and coated with Ilford L4 photographic emulsion. Emulsions were exposed for 14–21 days and then developed. Tissues were lightly counterstained with 1% toluidine blue.

RESULTS

Whole body scintographs were made of tumor bearing mice which had been injected intravenously with In-111 NTA small phospholipid particles 24 hr previously. EMT6 tumor images were clearly discernible in animals injected with neutral, negative and positively charged phospholipid vesicles. A comparison of the biodistribution of In-111 NTA delivery by each of these vesicle types can be made from the data presented in FIG. 1. As will be seen from the second column of FIG. 1, neutral phospholipid vesicles provided the best delivery of In-111 to tumor tissue. The specific targeting of the phospholipid vesicles to the tumors in this instance was at least as high as the targeting of the phospholipid vesicles to the liver or spleen, the usual target tissues of liposomes, and was nearly 8 times greater than the specific activity observed at the tumors when free In-111 NTA was injected in vivo. This will be seen from a comparison of the results shown in the first and second columns of FIG. 1. It can also be seen in FIG. 1 that, as liver and spleen uptake of In-111 decreases, the concentration of the phospholipid vesicles remaining in the blood increases. Also the increase in tumor associated radioactivity correlates approximately with the blood level of In-111.

Applicants have previously demonstrated a strong association with EMT6 tumor cells in vitro of liposomes with 6-aminomannose derivatives of cholesterol. Applicants accordingly attempted tumor imaging with phospholipid vesicles of aminomannose derivatives of cholesterol where such vesicles were labelled with In-111. Applicant's observations in this experiment confirmed that the vast majority of In-111 in such phospholipid vesicles ultimately is deposited in the liver and spleen. Tumor images could not be obtained with such phospholipid vesicles as demonstrated in columns 2 and 3 of FIG. 2 by the low deposition of the phospholipid vesicles in the tumor. The low deposition of the phospholipid vesicles in the tumor may result from the fact that most of such vesicles are taken up by the liver and spleen.

Liposomes with a lower concentration of the 6-AM derivative of cholesterol do not get trapped in the lung, so it seemed reasonable to assume that AM/2 vesicles (third column of FIG. 2) loaded with In-111 might be better tumor imaging agents than the material shown in the second column of FIG. 2. A comparison of the second and third columns of FIG. 2 shows that this was not the case. In fact, the AM/2 vesicles had a very high affinity for the liver and spleen. For example, after a period of 24 hours from the time of injection of the lipid vesicles in the blood stream, the combined radioactivity in the liver and spleen averaged greater than 75% of the total injected dose. This was the highest amount of liver and spleen uptake of vesicles observed of the several lipid composition studies.

Applicants have previously shown that positively charged liposomes were bound to EMT6 cells in vitro to a much greater extent than either neutral or negatively charged liposomes. Applicants accordingly investigated AML derivatives of cholesterol, another synthetic glycolipid derivative with positive charge. These AML liposomes did show a lower affinity for liver and spleen (Column 4 of FIG. 2) and a slightly increased uptake by tumor compared to that provided by AM/2 liposomes (column 2 of FIG. 2). However, this level of tumor-associated radioactivity was still three to ten times less than observed in the experiments with neutral, positive and negative liposomes as shown in FIG. 1.

In further experiments, applicants injected mice with either a saline solution or with 8 mg AM/2 liposomes. The saline solution provided a control and did not block the reticuloendothelial cells in the liver and spleen in the manner discussed above. This is shown in FIG. 3. The AM/2 liposomes provided a positive charge and were effective in blocking the reticuloendothelial cells in the liver and spleen. This is also shown in FIG. 3. Since the reticuloendothelial cells in the liver and spleen were blocked, any subsequent injection of phospholipid vesicles into the blood stream of the body had an increased opportunity to become targeted to the tumor.

One hour after the injection of the liposomes as discussed in the previous paragraph, 1 mg of the type of liposomes discussed above in relation to FIG. 1 was injected in the mice. These liposomes contained In-111. Twenty-four (24) hours afterwards, mice were sacrificed and dissected to determine the biodistribution of In-111.

FIG. 1 indicates the amount of In-111 targeted to the different parts of the body when phospholipid vesicles containing In-111 are introduced into the blood stream without any previous blockade of the reticuloendothelial cells in the liver and spleen. In contrast, FIG. 3 indicates the amount of In-111 targeted to the different parts of the body when phospholipid vesicles containing In-111 are introduced into the blood stream after a previous blockade of the reticuloendothelial cells in the liver and spleen. As will be seen, the amount of the In-111 targeted to the tumor significantly increased in most instances in FIG. 3 for the individual phospholipid vesicles more than for the corresponding phospholipid vesicles in FIG. 1. Furthermore, the amount of the In-111 received at the liver and spleen in FIG. 3 is significantly reduced from the amount of the In-111 received at the liver and spleen in FIG. 1.

As will be seen from a comparison of FIGS. 1 and 3, a significant amount of the phospholipid vesicles are targeted to the tumor even when the reticuloendothelial cells in the liver and spleen are not previously blocked. However, the amount of phospholipid vesicles targeted to the tumor is substantially increased when the reticuloendothelial cells in the liver and spleen are blocked before the phospholipid vesicles to be targeted to the tumor are introduced into the body.

In the experiments discussed above, the second group of phospholipid vesicles to be targeted to the tumor were introduced into the blood stream approximately one (1) hour after the introduction of the initial group of phospholipid vesicles into the blood stream to block the reticuloendothelial cells in the liver and spleen. It will be appreciated that other time periods than one (1) hour may also be used. For example, the time period may be considerably shorter than one (1) hour. Since the phospholipid vesicles blocking the liver and spleen are effective for an extended period, the introduction of the phospholipid vesicles to target the tumor may be considered as concurrent with the introduction of the phospholipid vesicles to block the liver and spleen.

As previously described, neutral DSPC:Ch phospholipid vesicles deliver In-111 to EMT6 murine tumors in sufficient quantity to allow definitive localization of tumors by gamma camera imaging. This tumor-associated specific radioactivity (% dose/gram tissue) is equal to levels achieved in liver and spleen, a finding which was not previously observed by others employing liposomes as tumor imaging agents.

In further experiments, applicants injected mice with free, unencapsulated In-111. NTA, and 24 hour biodistributions of radioactivity among various tissues were determined. (FIG. 1). Tumor uptake was compared to vesicle-encapsulated In-111-NTA. In all cases total tumor uptake was 40 to 50% less for the unencapsulated agents.

In the autoradiography studies, tumor sections produced many grains of exposure directly over the dense layer of rapidly growing EMT6 tumor cells at or near the surface of the tumor. In contrast, the inner necrotic core of the tumor produced little autoradiographic exposure. Adipocytes and connective tissue at the periphery of the tumor mass showed few grains of exposure.

Liver sections also showed high autoradiographic exposure as would be expected from the overall uptake of label. The uniform density of silver grains over the entire section of liver confirm that small vesicles are reaching hepatocytes, as has been reported by others. Spleen sections also showed much exposure as expected, but no distinct cell type could be identified as being responsible for the high spleenic labelling. Other tissues that were examined did not produce significant autoradiographic exposure.

Control tissue sections showed uniformly low photographic exposure, thus assuring that the experimental exposures obtained were not artifactual.

FIG. 5 indicates the distribution of radioactivity at various time points after injection of neutral vesicle-encapsulated In-111 NTA. This figure shows that tumor-associated radioactivity is maximal 24 hours after injection. Although blood clearance is rapid during the first few hours after injection a slower secondary clearance is then observed. Ninety percent of the radioactivity was cleared from the blood in 24 hours. While this suggests, that Indium-associated vesicles are selectively accumulating in the tumors over time, and circulating intact in the blood further studies were conducted to confirm this effect since an alternative explanation is that the vesicles are no longer intact and the NTA is binding to proteins in the blood.

Figure 6:
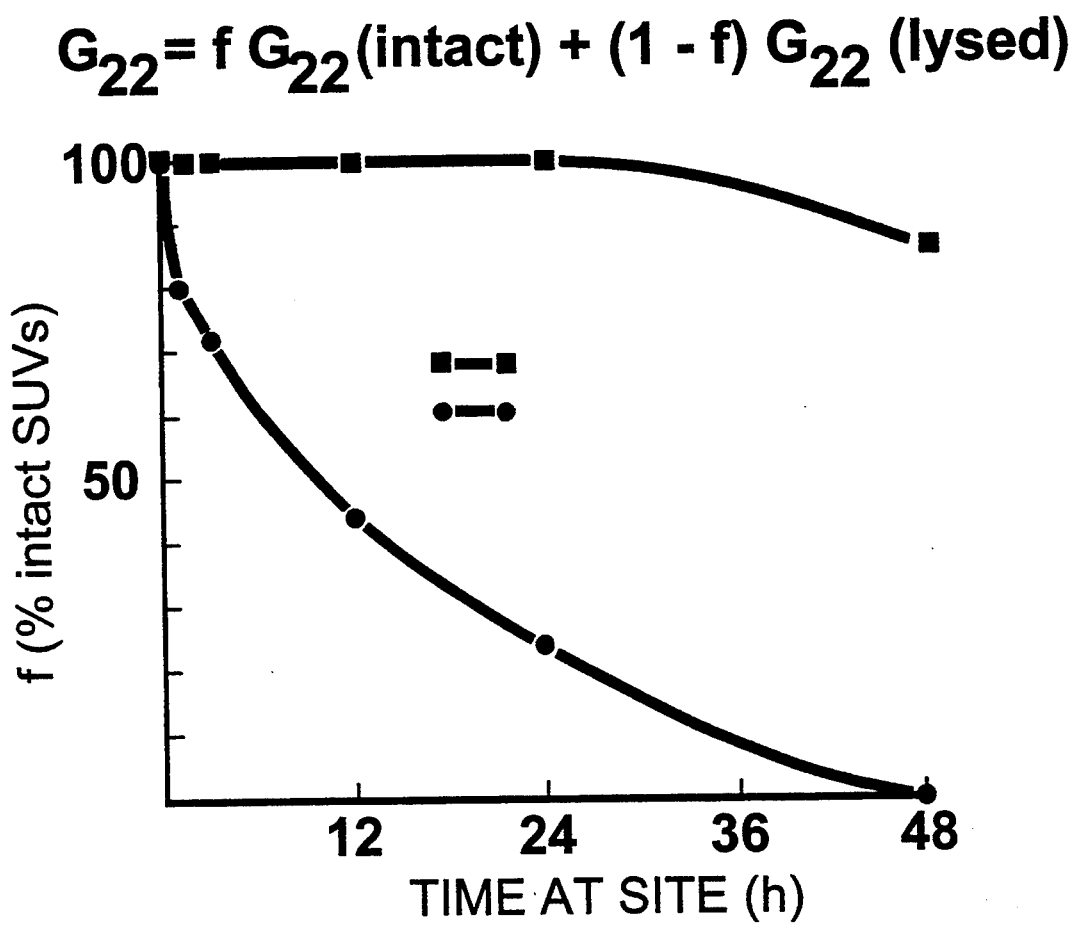
FIG. 6 is a graph indicating the percentage of intact labelled phospholipid vesicles remaining in blood and tumor as determined by perturbed angular correlation (PAC).
Figure 9A:
FIG. 9 is a series of photographs depicting tumor cells containing labelled vesicles.
Figure 9B:
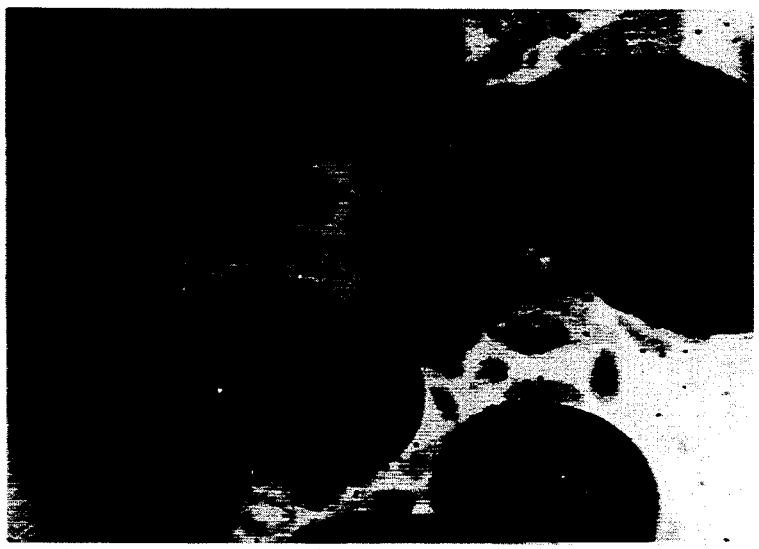
Figure 9C:
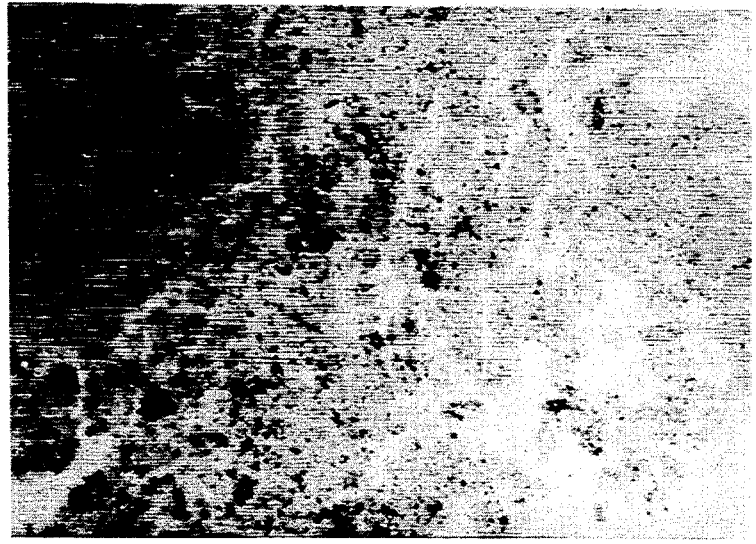

Applicants next performed perturbed angular correlation (PAC) studies on selected tissues at various time points (FIG. 6). Individual tumors, liver and blood samples were examined by gamma-ray PAC spectrometry at 1 to 48 hours after injection of Indium-111 labelled phospholipid vesicles. Results show that over 80% of the blood-born radioactivity remains within vesicles even after 48 hours. On the other hand, the time integrated perturbation factor for both liver and tumor decreased rapidly. This result indicates that the vesicles associated with tissues such as tumors are being broken down or lysed and that the Indium-111 is binding to macromolecules such as proteins, whereas vesicles in the blood are remaining intact over periods of time. As noted above, once bound to proteins inside cells Indium-111 remains fixed and is not excreted.

Applicants next examined the effect of labelling the membrane component rather than the internal aqueous space of the vesicles. Carbon 14-labeled phospholipid tracer was added to vesicles as 14C-DPPC in order to follow the biodistribution of the membrane component of the vesicles. Blood clearance and biodistributions within tissues are found to be similar to the experiments using In-111 labelling, especially during the early time points after injection. These results reinforce the conclusion that intact vesicles are reaching tumors using applicants methods.

Applicants next compared the biodistributions in tissues of free In-111-EDTA and vesicle-encapsulated In-111-EDTA. This set of experiments was performed to further demonstrate tumor localization of intact vesicles. EDTA is a strong chelator as compared to NTA, and will not release Indium-111 to be bound by proteins. Furthermore, unbound Indium-111 EDTA is rapidly cleared from the blood and excreted via the kidneys. Thus, radioactivity remaining in the animal 24 hours after injection must come from or still be within intact vesicles and not a protein bound intermediate. The results depicted in FIG. 7 show that at early time points encapsulated Indium-111 EDTA exhibits pharmacokinetics identical to C phospholipid labelling. Free In-111 EDTA however, does not accumulate significantly in any of the tissues listed in FIG. 7.

Finally, applicants performed biodistribution studies of vesicle-encapsulated Indium-111-NTA in mice bearing tumors of various types. (FIG. 8). Tumor associated radioactivity was at least 50% of the liver uptake on a per gram of tissue basis in seven of these tumor types. Lower relative tumor uptake was observed with choline adenocarcinoma 38, B-16 melanoma, and osteogenic sarcoma. These results suggest that many but perhaps not all tumor types will accumulate-encapsulated Indium-111.

There are several improvements in vesicle technology which are utilized in the present invention which may explain why better tumor imaging and delivery of vesicles into tumor cells are achieved. One such improvement is that In-111 is loaded into preformed liposomes. By this highly efficient method, specific activities of 200-300 uCi In-111/mg lipid have been obtained. Another improvement is that applicants have used highly purified phospholipid vesicles as discussed above.

A further improvement has been that In-111 has been encapsulated in the NTA complex. NTA is a relatively weak chelator and, in the presence of serum, NTA is displaced. Thus, when the phospholipid vesicles containing the In-111 is targeted to the tumor, the NTA becomes displaced by protein at the tumor. The In-111 becomes tightly associated with the protein at the tumor. Since this protein is within a cell, the In-111 is fixed at the position of the tumor. This circumstance provides two distinct advantages for the purposes of imaging. The first is that little radioactivity is lost due to leakage. After correcting for decay, applicants typically observed that 90% of the initial radioactivity remained in the animal at least twenty-four (24) hours after injection, based on the times required to accumulate a fixed number of counts with gamma counter. A second advantage is that when a label such as In-111 remains fixed at the site of liposome destruction, one can obtain information on rate, as well as total amount, of liposome uptake by the tissue.

Thus, the high tumor specific activities observed in this study are the result of a continuous accumulation of In-111 within the tumor over a twenty-four (24) hour period. By comparison, EDTA contained within vesicles forms a strong chelate in comparison to NTA. EDTA is not displaced at the tumor by proteins. Thus, the In-111 will not remain fixed within the cell. For example, when EDTA was chelated to In-111 in a phospholipid vesicle, only 25% of tumor specific activity was achieved, compared to In-111 NTA loaded liposomes.

The phospholipid vesicles as contructed herein may be used to provide an enhanced delivery of drugs or radionuclides to tumors in the body. This may be seen from the results of experiments specified in the table constituting FIG. 4. In these experiments [3H] Methotrexate (MTX) was injected directly into tumor-bearing mice as a control. The amount of the [³H] MTX directed to the tumors after a period of four (4) hours is illustrated in the row designated in FIG. 4 as "Free [³H] MTX".

Phospholipid vesicles containing DSPC:Ch:SA in the ratio of 4:1:1 were labelled with [14C] cholesterol oleate and the [³H]MTX was entrapped in the phospholipid vesicles. As will be seen, the amount of the phospholipid vesicles targeted to the tumors is almost three (3) times greater than the amount of the free MTX directed to the tumor.

The liver and spleen were also blocked in the manner described above and shown in FIG. 2 before the phospholipid vesicles containing DSPC:Ch:SA, as described in the previous paragraph, were targeted to the tumors. The last column of the table in FIG. 4 illustrates the targeting of these phospholipid vesicles to the tumors after the blocking of the liver and spleen. As will be seen, the amount of the phospholipid vesicles targeted to the tumors under such circumstances was almost the same as the amount discussed in the previous paragraph.

Finally, applicants have succeeded in demonstrating by autoradiography of ³H-labelled vesicles that vesicle-encapsulated chemotherapeutic agents such as methotrexate can be selectively delivered to tumor cells using the methods as described in the present invention.

Although this specification has been disclosed and illustrated with reference to particular applications, the principles involved are susceptible of numerous other applications which will be apparent to persons skilled in the art. The invention is, therefore, to be limited only as indicated by the scope of the appended claims.

We claim:

1. A method of placing a chemotherapeutic agent within a tumor for the treatment of the tumor comprising the steps of:
   (a) providing small micellular particles of less than 2000 Å comprising chemically pure phospholipid molecules;
   (b) incorporating a chemotherapeutic agent within the micellular particles; and
   (c) introducing said micellular particles with said chemotherapeutic agent therein into the bloodstream of the body to place intact said particles and said chemotherapeutic agent in the tumor.

2. A method according to claim 1 wherein said micellular particles constitute distearoyl phosphatidylcholine.

3. A method according to claim 2 wherein said micellular particles are in the form of spherical unilamellar phospholipid vesicles.

4. A method of placing a chemotherapeutic agent within a tumor in a body, comprising:
   (a) providing small micellular particles of less than 2000 Å comprising chemically pure phospholipid molecules;
   (b) modifying a portion of said phospholipid micellular particles to provide for the blockage of the reticuloendothelial cells in the body by such modified phospholipid micellular particles;
   (c) initially introducing the modified phospholipid vesicles into the bloodstream of the body to block uptake by the reticuloendothelial cells in the body;
   (d) incorporating a chemotherapeutic agent for treatment of the tumor into a second group of the micellular particles; and
   (e) subsequently introducing the second group of phospholipid micellular particles with said chemotherapeutic agent therein into the bloodstream of the body to place intact said particles and said chemotherapeutic agent within the tumor in the body.

5. A method according to claim 4 wherein said step of modifying a portion of the phospholipid micellular particles to block reticuloendothelial cells in the body comprises incorporating positively charged molecules into the phospholipid.

6. A method of placing a chemotherapeutic agent within a tumor in a body for the diagnosis or treatment of the tumor comprising the steps of:
   (a) providing a first group of micellular particles comprising chemically pure phospholipids having positively charged molecules incorporated therewith;
   (b) introducing such positively charged micellular particles into the bloodstream of the body to block reticuloendothelial cells in the body;
   (c) providing a second group of small micellular particles of less than 2000 Å comprising chemically pure phospholipid molecules having incorporated therein the chemotherapeutic agent for treatment; and
   (d) introducing said second group of micellular particles with the chemotherapeutic agent therein into the bloodstream of the body subsequent to the blocking of reticuloendothelial cells to place intact said particles and said chemotherapeutic agent within the tumor.

7. A method as defined in claim 6 wherein said positively charged molecules incorporated in said first group of micellular particles are amino group derivatives of cholesterol.

8. A method according to claim 7 wherein said positively charged molecules are aminomannose or aminomannitol derivatives of cholesterol.

9. A method according to claim 6 wherein said second group of micellular particles with the chemotherapeutic agent incorporated therein are neutral phospholipid particles.

10. A method as defined in claim 6 wherein said second group of micellular particles with the chemotherapeutic agent incorporated therein incorporate negatively charged molecules within the particles.

11. A method according to claim 10 wherein said negatively charged molecules are dicetyl phosphate.

12. A method according to claim 6 wherein said chemotherapeutic agent is methotrexate.

13. A method of placing a chemotherapeutic agent within a tumor comprising the steps of:
   (a) providing small micellular particles of less than 2000 Å comprising chemically pure neutral phospholipids;
   (b) adding cholesterol to such chemically pure neutral micellular particles;
   (c) incorporating a chemotherapeutic agent into such chemically pure neutral phospholipid micellular particles; and
   (d) introducing such small, chemically pure neutral phospholipid micellular particles into the body to place intact said particles and chemotherapeutic agents in the tumor in the body.

14. A method as defined in claim 13 wherein said chemotherapeutic agent is methotrexate.

15. The method of claims 1, 4, or 5 including the step of incorporating cholesterol into such micellular phospholipid particles or molecules.

16. The method of claim 3 in which distearoyl phosphatidylcholine and cholesterol are included in said particles in a 2:1 molar ratio.

17. The method of claims 1, 4, 6, or 13 in which said micellular particles incorporating said chemotherapeutic agent are phospholipid vesicles and said vesicles are delivered in tact to the tumor cells.

* * * * *

UNITED STATES PATENT AND TRADEMARK OFFICE

CERTIFICATE EXTENDING PATENT TERM
UNDER 35 U.S.C. § 156

PATENT NO.      :   5,441,745

ISSUED          :   August 15, 1995

INVENTOR(S)     :   Cary A. Presant et al.

PATENT OWNER    :   NeXstar Pharmaceuticals, Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

238 days from May 28, 2008, the original expiration date of the patent, subject to the payment of maintenance fees as provided by law, with all rights pertaining thereto as provided by 35 U.S.C. § 156(b).

I have caused the seal of the Patent and Trademark Office to be affixed this 27th day of February 1998.

Bruce A. Lehman
Assistant Secretary of Commerce and
  Commissioner of Patents and Trademarks